United States Patent [19]

Bonnefous et al.

[11] Patent Number: 4,803,990
[45] Date of Patent: Feb. 14, 1989

[54] EXAMINING MOVING OBJECTS BY ULTRASOUND ECHOGRAPY

[75] Inventors: Odile M. A. Bonnefous, Nogent-Sur-Marne; Patrick R. Pesque, Perigny, both of France

[73] Assignee: U.S. Philips Corporation, New York, N.Y.

[21] Appl. No.: 900,296

[22] Filed: Aug. 25, 1986

[30] Foreign Application Priority Data

Dec. 3, 1985 [FR] France ................................ 85 17851
Mar. 25, 1986 [FR] France ................................ 86 04225

[51] Int. Cl.$^4$ .............................................. A61B 10/00
[52] U.S. Cl. ............................ 128/661.08; 73/861.25
[58] Field of Search ...................... 128/663; 73/861.25

[56] References Cited

U.S. PATENT DOCUMENTS 4,583,409  4/1986  Lannuyel et al. ............... 128/663 X
4,622,977  11/1986 Namekowa et al. .................. 128/663
4,641,668  7/1987  Namekowa ......................... 128/663

OTHER PUBLICATIONS

Dotti et al, "Bloodflow Measurements by Ultrasound Correlation Techniques" Energia Nuclease, vol. 2–3, No. 11, Nov. 1976.
Bassini et al, "In Vivo Recording of Blood Velocity Profiles and Studies in Vitro of Profile Alterations Induced by Known Stenoses," Tepos Hrt Jrnl. vol. 9 #2 Jun. 1982.
Bossini et al, "Ultrasonic Non-Invasive Blood Flow Meter Based on Cross Correlation Techniques", Ultrasonic Itnl Syrp., 1979.

Primary Examiner—Francis J. Jaworski
Attorney, Agent, or Firm—Jack E. Haken

[57] ABSTRACT

An apparatus for scanning moving objects, notably flowing blood, by means of ultrasound echography in order to determine movement parameters of such objects. The apparatus comprises at least one ultrasound transducer which is connected to a stage for the periodic transmission of a pulse signal having a predetermined recurrent frequency $F=1/T$ and to a stage for receiving echograpic signals returned to the transducer and for processing the signals received. In accordance with the invention, the apparatus is characterized in that it comprises a digital processing channel which is successively composed of a circit (320) for suppressing fixed echoes, a circuit for estimating flow parameters, a discriminator circuit (360), a device (370) for storage, scan conversion and color encoding, and a display device (312).

4 Claims, 5 Drawing Sheets

EXAMINING MOVING OBJECTS BY ULTRASOUND ECHOGRAPY

The invention relates to an apparatus for scanning moving objects, notably flowing blood, by means of ultrasound echography in order to determine movement parameters of such objects, which apparatus comprises at least one ultrasound transducer which is connected to a stage for the periodic transmission of a pulse signal having a predetermined recurrent frequency $F=1/T$ as well as to a stage for receiving echographic signals returned to the transducer and for processing the signals received.

For a number of years pulsed-wave ultrasound Doppler systems have been used for measuring the velocity of blood flow at a given point, or at least the projection of this velocity on the axis of the beam emitted by the ultrasound transducers. More recently apparatus have appeared which enable real-time determination of the flow velocity along the path followed by the ultrasound wave and even across the sectional plane obtained by way of a scanning motion of the transducer. The majority of these systems utilize the frequency shift or the phase shift of the signal returned by the moving targets in order to derive the axial velocity of the blood flow therefrom.

For example, European Patent Application No. 0092841 relates to such an apparatus. The apparatus described therein utilizes the measurement of the phase shift between the successive echoes returned by the moving targets in reaction to a recurrent excitation. However, the use of the pulsed Doppler frequency shift or phase shift method is restricted notably by a phenomenon which is referred to as "aliasing" or biased determination and which prevents the estimation of velocities whose absolute value exceeds a given limit which is defined as $V_{lim}=(c/4)\cdot(F/f_c)$, where c is the speed of propagation, F is the recurrent frequency of the exitation, and $f_c$ is the central frequency of the echographic signal. This phenomenon is described notably in "Doppler Ultrasound and Its Use in Clinical Measurement" by P. Atkinson and J. P. Woodcock, Academic Press, 1982, Chapter III, section 3.3d.

Moreover, the apparatus for performing this known method utilizing the phase shift are subject to a restriction imposed by an indeterminacy relation which links the axial resolution $\Delta z$ and the measurement accuracy of the velocity $\Delta V/V$ to the wavelength $\lambda$:

$$(\Delta V/V)\cdot \Delta z = \lambda/2 \qquad (1).$$

This relation, stated in chapter II, section 2, 3a of the cited publication (relation 2.30) thus imposes a compromise between the axial resolution and the accuracy of the velocity measurement; this is not compatible with the desired exact measurement of a velocity profile or an image of flowing blood.

It is an object of the invention to provide an apparatus of the kind set forth in which this limitation of the velocity measurement range is eliminated and in which the accuracy of the velocity measurement increases as the axial resolution increases.

To this end, the apparatus in accordance with the invention is characterized in that it comprises a digital processing channel which is successively composed of a circuit for suppressing echoes which originate from stationary objects and which are referred to as "fixed" echoes, a circuit for estimating flow parameters, a discriminator circuit, a device for storage, scan conversion and colour encoding, and a display device.

In the set-up in accordance with the invention there is obtained a type of signal processing in the time domain wherein the returning of ultrasound signals is no longer interpreted in terms of frequency shift or phase shift, but rather in terms of a progressive shift in time of the echographic signals after each transmission of pulse signals. This set-up actually utilizes a new principle of real-time estimation of flow parameters which is based on the formulation in time of the ultrasound signals returned by the moving targets. The echographic signals successively obtained in reaction to the recurrent excitations of the fixed transducer can be expressed as:

$$e_{i+1}(t) = e_i(t - \tau(t)) \qquad (2)$$

where i is the rank of the echographic line and $\tau(t)$ represents the time shift induced by the displacement of the targets between two activations. The shift is related to the local axial velocity $V_Z(t)$ (projection on the propagation axis Z of the ultrasound wave) by the relation:

$$\tau(t) = 2 \cdot \frac{V_z(t)}{c} \cdot T \qquad (3)$$

where c is the speed of propagation of the ultrasound waves and T is the recurrent period of the excitations. The localization of the flow velocity is represented by the conventional echographic relation linking the time t to the depth Z:

$$z = \tfrac{1}{2}\cdot ct \qquad (4).$$

The use of correlation functions enables the measurement of the time shifts between signals (see the article "The generalized correlation method for estimation of time delay", C. H. Knapp and G. C. Carter, IEEE Transactions on Acoustics, Speech and Signal Processing, Vol. ASSP-24, No. 4, 1976). When applied to echography, the intercorrelation function between $e_i$ and $e_{i+1}$ is:

$$f_i(t_o, u) = \int_{t_o}^{t_o + w} e_i(t) \cdot e_{i+1}(t + u)\, dt. \qquad (5)$$

The axial component of the flow velocity, averaged over the resolution cell defined by the time window having a length W and the width of the ultrasound beam, is found by determining the time shift u for which the correlation function $f_i$ has a maximum value. The time shift which results in a maximum value of $f_i$ equals $\tau(t_o)$, which is the mean value of the shifts $\tau(t)$ across the window $(t_o, t_o+W)$, thus enabling measurement of the local mean flow velocity by way of the relation (3).

On the other hand, it appears that the local variation of the flow velocity $\sigma^2(t_o)$ in the resolution cell is proportional to the quantity defined by:

$$\left(1 - \frac{f_i(t_o), \tau(t_o)}{E_i(t_o)}\right)^{\tfrac{1}{2}} \qquad (6)$$

where $E_i(t_o)$ is the energy of the echographic signal in the window $(t_o, t_o+W)$:

$$E_i(t_o) = \int_{t_o}^{t_o + w} e_i^2(t) \cdot dt. \tag{7}$$

It will be apparent from the foregoing expressions that the principle of the invention, being based on the determination of flow parameters by a correlation function, eliminates the limitations of previous methods. Actually, the time shift $\tau$ can be unambiguously estimated, regardless of its value. As a result, the range of speeds which can be measured is no longer limited. On the other hand, because the processing is based on the measurement of the time shift of the successive echoes caused by the changing positions of the targets, it will be apparent that a high axial resolution enables exact determination of the position of the targets and even permits exact measurement of their displacement and hence of their speed, which was not possible by means of the previous methods, considering the indeterminacy relation mentioned above.

In the apparatus in accordance with the invention, which may further comprise a conventional analog processing channel for the display of slices scanned according to the conventional echographic principle, the circuit for suppressing fixed echoes preferably comprises successively an analog-to-digital converter which is controlled by control signals at the sampling rate with a frequency $f=1/\Delta t$, and a subtractor which receives on its first input, having a given sign, directly the output signal of the converter and on its second output, having the opposite sign, the same output signal which, however, has been delayed by an integer number of sampling periods $\Delta t$ in a delay circuit, said subtractor supplying a signal which is referred to as a difference signal. The difference signal thus supplied is used in the circuit following the estimation of flow parameters as well as in the discriminator circuit.

The circuit for estimating flow parameters in a first embodiment comprises a correlation circuit which supplies, on the basis of said difference signals relating to two successive echographic lines, a predetermined number of correlation function values, and an interpolation circuit which supplies, on the basis of said values, parameters which are representative of the velocity of the objects scanned along the axis of propagation of the ultrasound waves.

The correlation circuit in general comprises an odd number $(2I+1)$ of parallel channels, each of which is composed of a correlator which is controlled by said control signals having the sampling frequency F, said $(2I+1)$ correlators receiving directly on a first input said difference signal supplied by the circuit for suppressing fixed echoes, and on a second input the same signal which, however, has been delayed via delay lines introducing $(2I+1)$ distinct delays $T-I\Delta t$, $T-(I-1)\Delta t$, $(T-(I-2)\Delta t, \ldots, T-\Delta t, T+\Delta t, \ldots,$ $T+(I-2)\Delta t$, $T+(I-1)\Delta t$, $T+I\Delta t$, and supplying $(2I+1)$ correlation function values, said correlators preferably being 1-bit correlators which are advantageously associated with a linear interpolation circuit. Mean value calculating circuits are preferably included in each of the $(2I+1)$ parallel channels of the correlation circuit in which they are connected to the output of the correlators.

However, it is to be noted that the above relation (2) also holds good for signals obtained when only the sign of the echographic signals corresponding to the echographic lines is taken into account, so that:

$$\begin{aligned} s_{i+1}(t) &= \text{sign of } (e_{i+1}(t)) \\ &= \text{sign of } (e_{i+1}(t - \tau(t))) \\ &= s_i(t - \tau(t)) \end{aligned} \tag{8}$$

The information contained in these signals reduced to the sign $s_i(t)$ actually suffices for locally estimating mean velocities, because it appears that the ascending or descending edges of such a signal $s_{i+1}(t)$ are replicas, delayed by $\tau(t)$, of the preceding signal $s_i(t)$. Thus, an estimation $\tau$ or $\tau(t)$ is available for each ascending or descending edge of the signal $s_i$ by measurement of the time shift between this ascending or descending edge and the corresponding edge of the next signal $s_{i+1}$. Thus, information will be available in all half-periods of the echographic signal.

It has been found that a 1-bit multiplication is very suitable for the measurement of $\tau$: when the signals are different, the result of the 1-bit multiplication will be 0; it will be 1 when the signals are identical. Thus, the following function $f_i(t_o)$:

$$f_i(t_o) = \frac{1}{w} \int_{t_o}^{t_o + w} s_i(t) \cdot s_{i+1}(t) \cdot dt \tag{9}$$

where $t_o$ and $t_o+w$ define a time window having a length w, verifies the relation:

$$\begin{aligned} f_i(t_o) &= 1 - 2\nu_o |\hat{\tau}(t_o)| \\ &= 1 - 4\nu_o T|\hat{V}(t_o)|/c \end{aligned} \tag{10}$$

where $\hat{V}$ is the estimated velocity and $\nu_o$ is the central frequency. Actually, by means of this calculation only the amplitude of the velocity can be obtained and not its direction which, however, represents very important user information.

In order to eliminate this ambiguity as regards the direction of the velocity, it must be considered that $f_i(t_o)$ is the value taken as 0 by the local correlation function and defined by:

$$C(t_o,u) = \frac{1}{w} \int_{t_o}^{t_o + w} s_i(t) \cdot s_i + 1(t + u) \cdot dt \tag{11}$$

This function has the following properties. On the one hand, if the velocity is positive, $\tau(t)$ is larger than 0 and the expression:

$$C(t_o,u) = \frac{1}{w} \int_{t_o}^{t_o + w} s_i(t) \cdot s_i(t + u - \tau) \cdot dt$$

is an increasing function in the vicinity of $u=0$, whilst the same expression $C(t_o,u)$ is a decreasing function in the vicinity of $u=0$ if the velocity is negative. On the other hand, in the vicinity of the correlation, peak $C(t_o,u)$ is triangular.

Thus, the calculation of the slope A of $C(t_o,u)$ in the vicinity of $u=0$ enables determination of the direction of the velocity as well as of the value of the correlation peak $C_{max}$. This value can actually be used for estimating the variation $\sigma$ of the velocity according to the relation:

$$\sigma \approx (1 - C_{max})^{\frac{1}{2}} \quad (12)$$

$C_{max}$ is actually calculated as follows:

$$\begin{aligned} C_{max} &= C(t_o, 0) + |A||\hat{\tau}| \quad (13) \\ &= C(t_o, 0) + |A|(1 - C(t_o, 0))/2v_o \text{ or:} \\ C_{max} &= (1 - |A|/2v_o) \cdot C(t_o, 0) + \left|\frac{A}{2v_o}\right| \end{aligned}$$

A processing unit comprising a 1-bit correlator having three calculation channels and a calculation unit will thus provide an estimation of the parameters V and $\sigma_V$.

In a second embodiment, the circuit for estimating flow parameters comprises a correlation circuit which supplies, on the basis of said difference signals relating to two successive echographic lines, three correlation function values, and an arithmetic unit which supplies, on the basis of said values, parameters which are representative of the velocity of the objects scanned along the axis of propagation of the ultrasound waves.

The correlation circuit then comprises three parallel channels, each of which is composed of a 1-bit correlation which is controlled by said control signals at the sampling frequency F, said correlators receiving directly on a first input said difference signal supplied by the circuit for suppressing fixed echoes, and on a second input the same signal which, however, has been delayed via delay lines which introduce three distinct delays $T - \Delta t$, $T$, $T + \Delta t$, and supplying three correlation function values. Preferably, mean value calculating circuits are again inserted in each of the three parallel channels in which they are connected to the output of the correlators.

In the proposed embodiments, the discriminator circuit preferably comprises successively a circuit for squaring the difference signal supplied by the circuit for suppressing fixed echoes, a summing device for calculating the local energy of the difference signal, and a circuit for validating/rejecting the output signals of the circuit for estimating the flow parameters, depending on the calculated value of said local energy. Moreover, the discriminator circuit is preferably provided with a further circuit for validating/rejecting the flow parameters, depending on the value of at least one of these parameters.

The particularities and advantages of the invention will be described in detail hereinafter with reference to the accompanying drawings which are given by way of example; therein:

Figure 1:
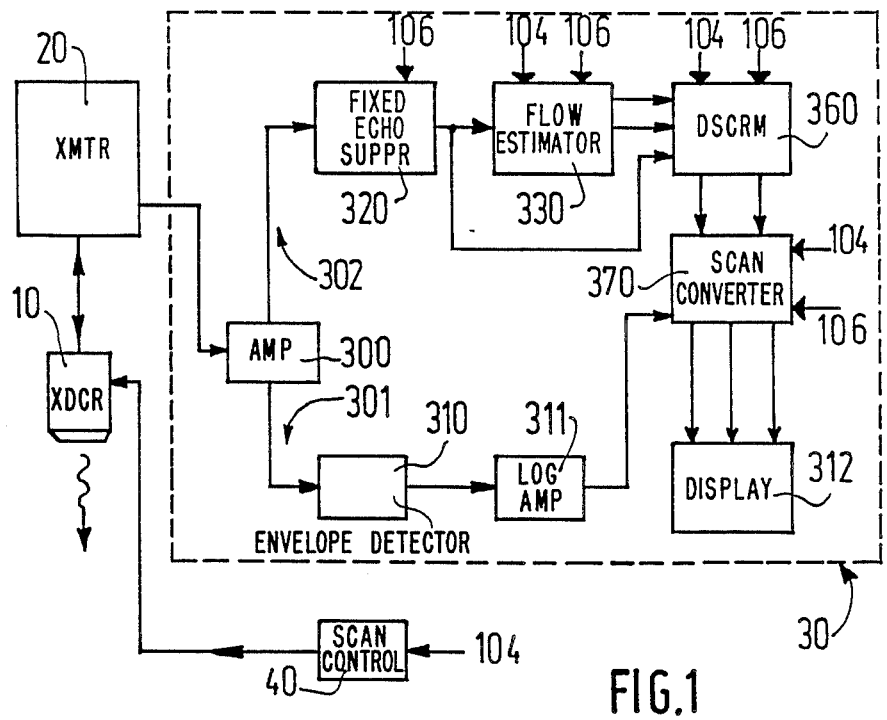
FIG. 1 shows a preferred embodiment of the apparatus in accordance with the invention.

The apparatus shown in FIG. 1 comprises in known manner an ultrasound transducer 10 which is connected to a transmitter stage 20, to a stage 30 for receiving and processing, as well as to a device 40 for mechanically controlling the scanning motion of a transducer. Instead of this transducer, however, use could alternatively be made of an array of transducers associated with a device for electronic scanning control.

Figure 2:
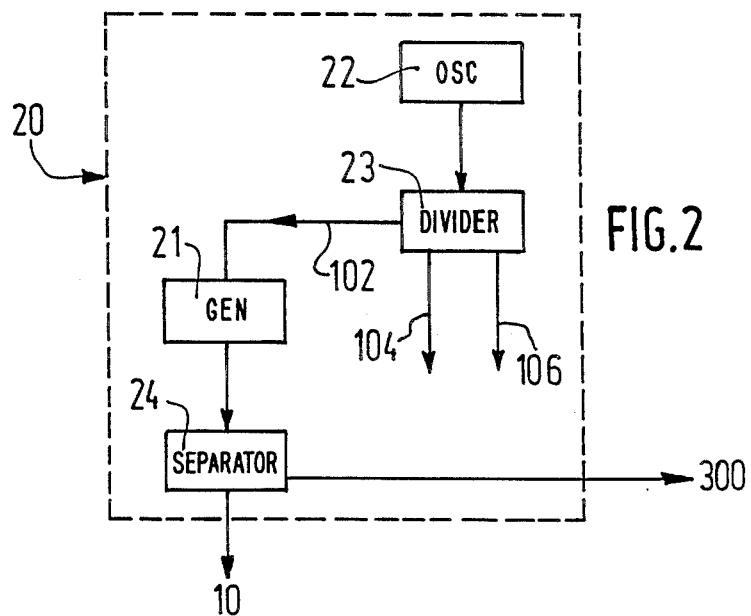
FIGS. 2 and 3 show typical embodiments of the transmitter stage and the circuit for suppressing fixed echoes, respectively, of this apparatus.

In the embodiment which is described in more detail with reference to FIG. 2, the transmitter stage 20 comprises a generator 21 for electric excitation signals which are applied to the transducer 10 which converts these signals into periodic trains of ultrasound pulse signals. Transmission is controlled by clock signals which are available on a connection 102 and which are supplied with a predetermined recurrent frequency F (for example, in the order of 5 kHz) by a sequencer which comprises successively an oscillator 22, in this case having a frequency of 32 MHz, and a frequency divider 23. The divider supplies the clock signals on the connection 102 as well as other respective control signals on the connections 104 and 106, the latter signals having a frequency of 1 kHz and 16 MHz, respectively in the present embodiment. The control signals present on the connection 104 control notably the device 40 for the scanning motions of the transducer. A separator 24 for separating the transmitter stage 20 and the receiving and processing stage 30 is inserted between the transducer 10, the generator 21 and the stage 30 and prevents the saturation of the receiving circuits by the signals transmitted.

The receiving and processing stage 30 includes, connected to the output of the separator 24, a high frequency amplifier 300 which provides gain compensation as a function of the depth, followed by two processing channels 301 and 302 which are connected in parallel. The channel 301 is of a conventional type and comprises, in the present embodiment, a series connection of an envelope detector 310, a logarithmic compression amplifier 311, a storage and scan conversion device 370 which also has a colour encoding function, and a display device 312. The channel 301 enables grey-scale images to be formed of object slices scanned according to the conventional echographic principle.

In accordance with the invention, the channel 302 comprises a series connection of a circuit 320 for suppressing fixed echoes, a circuit 330 for estimating flow parameters, a discriminator circuit 360, the device 370 for storage, scan conversion and colour encoding, and the display device 312.

Figure 3:
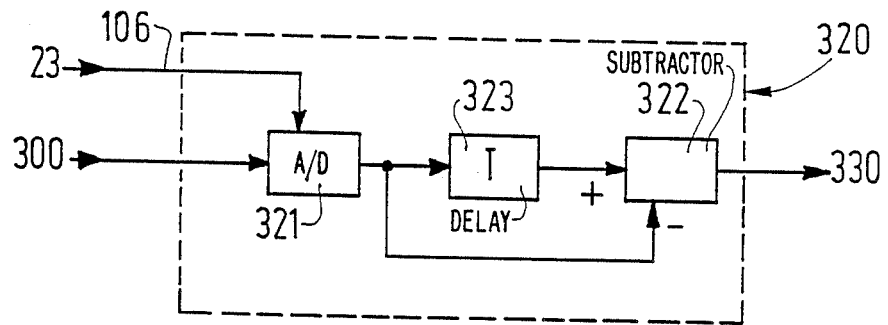

In the embodiment shown in FIG. 3, the digital circuit 320 for suppressing fixed echoes itself includes an analog-to-digital converter 321 whose output is connected on the one hand directly to the negative input of a subtractor 322 and on the other hand to the positive input of this subtractor via a delay circuit 323. The delay imposed by the circuit 323 could amount to several periods $T = 1/F$, but is preferably as short as possible and equal to T. The circuit 320 is provided in order to eliminate all fixed echoes, notably those which are caused by reflection of the ultrasound waves from the walls of arteries in which the flow being studied occurs. The presence of these fixed echoes is disturbing because their amplitude is much higher (in the order of +40 dB in the case of blood flow) than that of the useful signals, that is to say the signals which are returned by the moving targets. The circuit 320 is also controlled, via the connection 106, by the frequency divider 23 of the sequencer which applies the 16 MHz sampling control signal thereto.

Figure 4:
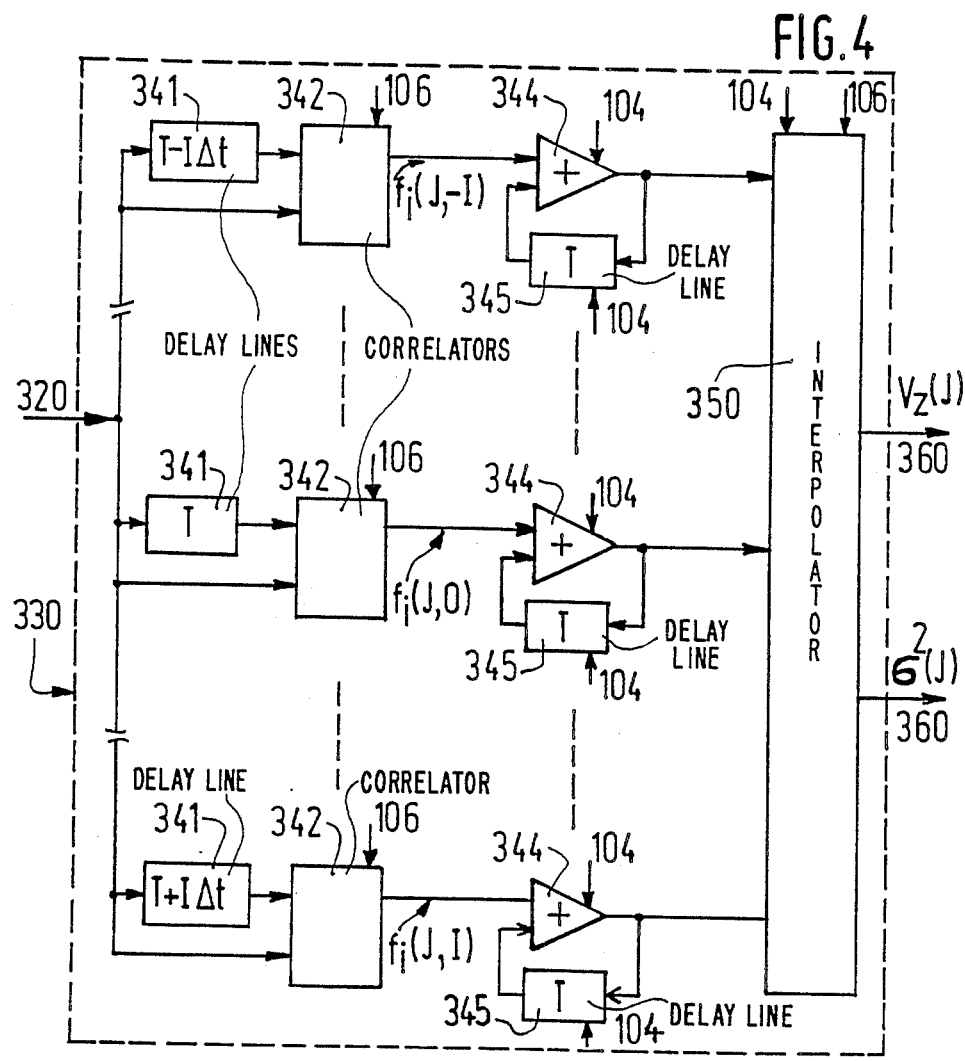
FIG. 4 shows a first embodiment of the circuit for estimating flow parameters.

In a first embodiment as shown in FIG. 4, the circuit 330 for estimating flow parameters includes a correlation circuit and an interpolation circuit. On the basis of the difference signals between two successive echographic lines of samples $d_i(t)$, $d_{i+1}(t)$ etc. . . . (where i represents the rank of this signal) which are successively supplied by the circuit 320 for suppressing fixed echoes, the correlation circuit supplies correlation function values, in this case an odd number (2I+1). On the basis of these (2I+1) values, the interpolation circuit supplies parameters which characterize the different flows encountered along the axis of propagation of the ultrasound wave. In the present case these parameters are the axial component of the local mean velocity $V_z$ and the local variation $\sigma^2$ thereof; in this context the word local is used so as to indicate the location in the depth along said axis of propagation Z.

The correlation circuit in the present embodiment includes (2I+1) correlators 342, a first input of which directly receives the output signal $d_{i+1}(t)$ of the circuit 320 for suppressing fixed echoes, whilst a second input thereof receives the same output signal of the circuit 320, be it that the latter signal has been delayed by delay lines 341 so that it corresponds to the preceding signal $d_i(t)$. Moreover, in order to enable calculation of the (2I+1) correlation function values, each of the lines 341 presents a distinct delay, that is to say (2I+1) values from $T-I\Delta t$ to $T+I\Delta t$, where $\Delta t$ represents the sampling period imposed by the connection 106.

This calculation of the (2I+1) correlation function values, performed in parallel, utilizes K successive samples of the two input signals of the correlators. The groups of K samples define successive time windows which have a length $K\Delta t$ and which are progressively shifted in the rhythm of the frequency imposed by the connection 106. The correlation function is defined by an expression of the type:

$$f_i(J,P) = \sum_{k=1}^{k=K} d_i((k + J)\Delta t) \cdot d_{i+1}((k + J + P)\Delta t) \quad (14)$$

where:

J determines the start of the time window having a length $K\Delta t$;

P represents the time shift introduced between $d_i$ and $d_{i+1}$ for which the correlation function value is calculated (P varying from $-I$ to $+I$ in steps of 1);

i represents the rank of the difference between two successive echographic lines $e_i$ and $e_{i+1}$.

Figure 5:
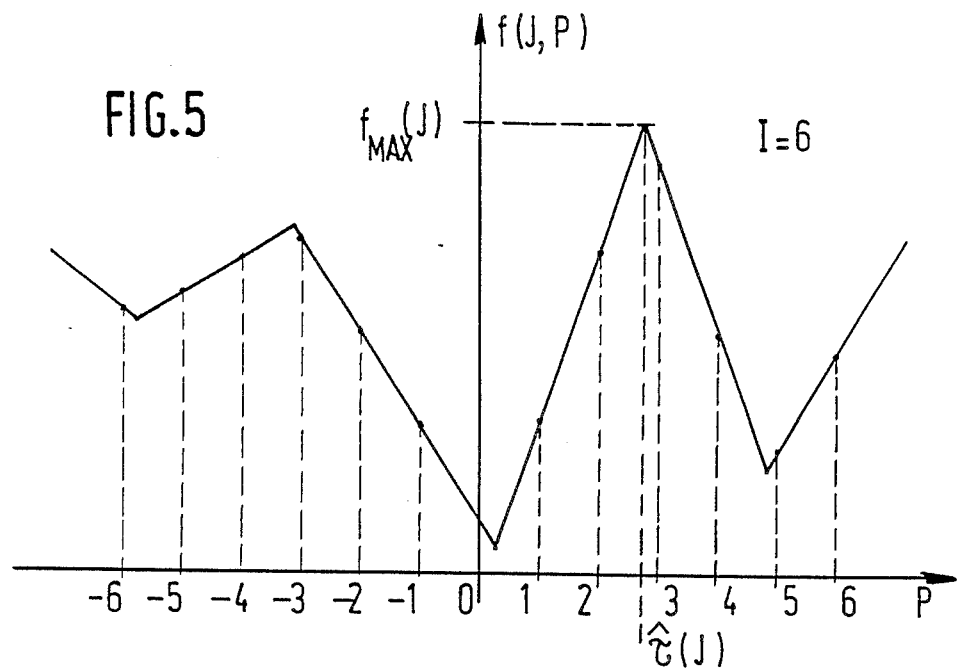
FIG. 5 illustrates, for the above embodiment, the operating principle of the interpolation circuit, that is to say a linear interpolation circuit for the calculation of $(2I + 1) = 13$ correlation function values.

The correlators 342 are controlled via the output connection 106 of the frequency divider 23 of the sequencer and are preferably formed by 1-bit correlators which offer several advantages: on the one hand, the execution of the correlation method is simplified, whilst on the other hand the principal correlation peak obtained is shaped as a triangle which is very suitable for linear interpolation; finally, nowadays inexpensive 1-bit integrated circuit correlators are readily available (for example, the correlators TDC 1023 from TRW, La Jolla, CA 92038 USA). Therefore, when the described embodiment includes such 1-bit correlators, the interpolation circuit 350 will generally be a linear interpolation circuit. For example, for I=6 FIG. 5 shows the 13 correlation function values obtained as well as the interpolated value corresponding to the amplitude of the apex of the principal correlation peak. In FIG. 4 the correlation function is denoted by $f_i(J, -I)$ for the first correlator, $f_i(J, -(I-1))$ for the next correlator (not shown), . . . , $f_i(J,0)$ for the $(I+1)^{th}$ correlator, etc. . . . , and $f_i(J,I)$ for the $(2I+1)^{th}$ correlator.

The interpolation circuit may be formed by a programmed arithmetic unit which comprises a microprocessor, or preferably by a wired arithmetic unit. This interpolation circuit operates as follows: during a first period the maximum value is selected from the (2I+1) correlation function values; with this value there are associated the two adjacent correlation function values and these three values enable the reconstruction of the principle isosceles correlation peak. The abscissa $\hat{\tau}(J)$ of the principal correlation peak enables determination of the local velocity $V_z$ at the depth $z_0 = (cJ\Delta t)/2$ by multiplication according to the relation:

$$V_Z(z_o) = c \cdot \frac{\hat{\tau}(J)}{2T} \quad (15)$$

and the amplitude $f_{MAX}$ of this peak enables determination of the variation $\sigma^2(z_o)$ according to the relation:

$$\sigma^2(z_o) = A \left( 1 - \frac{f_{MAX}(J)}{K} \right) \quad (16)$$

where A is a proportionality factor.

Between the (2I+1) correlators and the (2I+1) corresponding inputs of the interpolation circuit 350 there are preferably provided (2I+1) mean value calculating circuits which are actually formed by accumulators, each of which comprises an adder 344 and a delay line 345 for a delay T (or a multiple of T). These mean value calculating circuits enable accumulation of the correlation function values on N successive echographic lines and the formation of the mean value thereof before supply to the interpolation circuit. The adders 344 and the delay lines 345 are connected to the sequencer (22, 23) via the connection 104 in order to be reset to zero at regular intervals $N \times T$. The frequency of the resetting to zero, imposed by the connection 104, is that of the signals present on the connection 102, divided by N.

Figure 6:
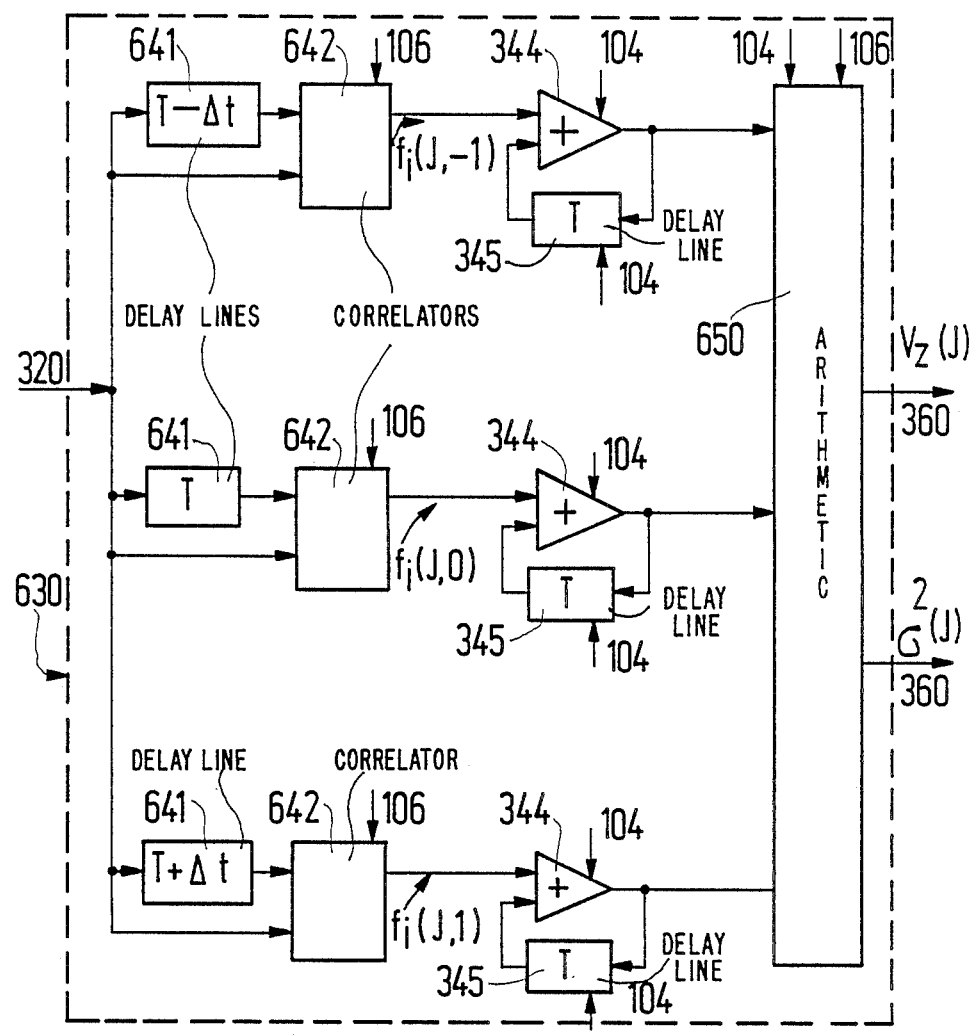
FIG. 6 shows a second embodiment of the circuit for estimating flow parameters.
Figure 7A:
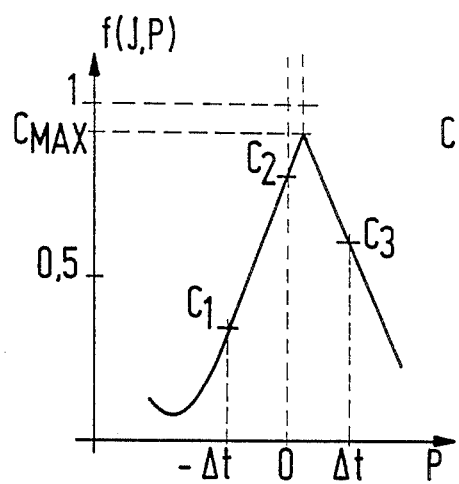
FIG. 7 illustrates, for this embodiment, the operating principle of the arithmetic unit.
Figure 7B:
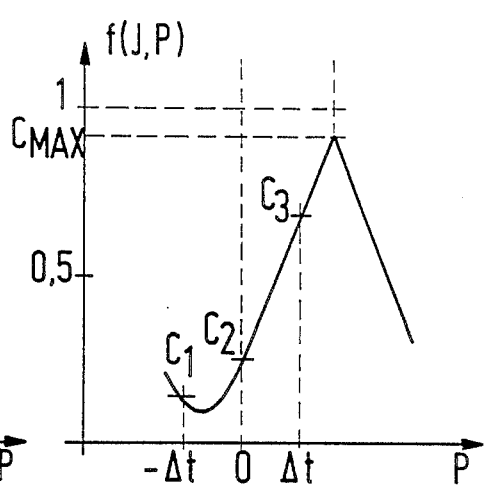
Figure 7C:
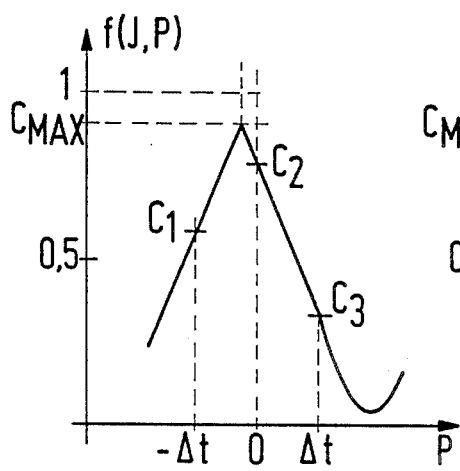
Figure 7D:
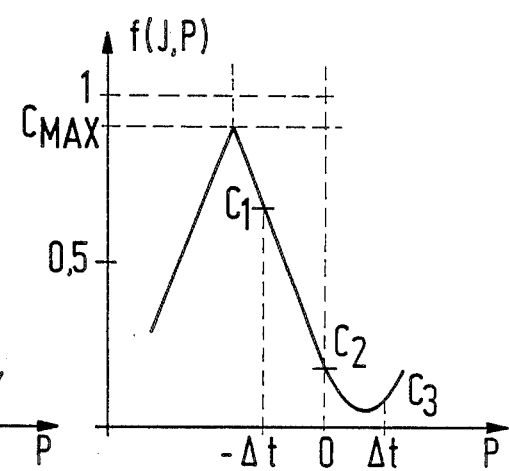

In a second embodiment as shown in FIG. 6, the circuit for estimating the flow parameters (now denoted by the reference numeral 630) comprises a correlation circuit and an arithmetic unit 650. On the basis of the difference signals between two successive echographic lines of samples $d_i(t)$, $d_{i+1}(t)$ etc. . . . (where i represents the rank of this signal) which are successively supplied by the circuit 320 for suppressing fixed echoes, the correlation circuit supplies three correlation function values. On the basis of these three values, the arithmetic unit supplies parameters which characterize the different flow encountered along the axis of propagation of the ultrasound wave. In the present case these parameters are the axial component of the local mean velocity $V_z$ and the local variation $\sigma^2$ thereof; in this context the word local is used so as to indicate the location in the depth along said axis of propagation Z.

The correlation circuit 630 notably comprises three correlators 642, a first input of each of which directly receives the output signal $d_{i+1}(t)$ of the circuit 320 for suppressing fixed echoes, whilst a second input thereof receives the same output signal of the circuit 320, be it that the latter signal has been delayed by delay lines 641 and hence corresponds to the preceding signal $d_i(t)$. Moreover, in order to allow for calculation of the three correlation function values, each of the lines 641 presents a distinct delay, so three values $T-\Delta t$, $T$, $T+\Delta t$, where $\Delta t$ represents the sampling period imposed by the connection 106.

The calculation of the three correlation function values, being performed in parallel, utilizes K successive samples of the two input signals of the correlators. The groups of K samples define successive time windows which have a length $K\Delta t$ and which are progressively shifted in the rhythm of the frequency imposed by the connection 106. The correlation function is defined as before by the expression (14). The correlators 642 are controlled via the output connection 106 of the frequency divider 23 of the sequencer and are formed by 1-bit correlators. the arithmetic unit 650 may be a programmed arithmetic unit which comprises a microprocessor, or preferably a wired arithmetic unit. The arithmetic unit has three correlation function values available:

$$C_1 = C(t_o, -\Delta t) \quad (17)$$

$$C_2 = C(t_o, 0) \quad (18)$$

$$C_3 = C(t_o, \Delta t) \quad (19).$$

The sign of the slope of the correlation function with which the direction of the velocity corresponds is determined by:

$$s = \text{sign}(C_3 - C_1) \quad (20).$$

Using the relation 7, the velocity is given by the expression:

$$\hat{V} = s \cdot \frac{C_1 - C_2}{4 v_o T}. \quad (21)$$

The value A of the slope at 0 of the correlation function is obtained according to the following table:

|  | $C_2 \geq 0.5$ | $C_2 < 0.5$ |
| --- | --- | --- |
| $C_3 - C_1 \geq 0$ | $A = (C_2 - C_1)/\Delta t$ | $A = (C_3 - C_2)/\Delta t$ |
| $C_3 - C_1 < 0$ | $A = (C_3 - C_2)/\Delta t$ | $A = (C_2 - C_1)/\Delta t$ |

This table contains, in association with the corresponding FIGS. 7a to 7d, four types of possible configurations describing the values $C_1$, $C_2$, $C_3$. Therefrom, the value $C_{MAX}$ of the correlation peak is derived:

$$C_{MAX} = \left(1 - \frac{|A|}{2v_o}\right) \cdot C_2 + \frac{|A|}{2v_o} \quad (22)$$

as well as the variation:

$$\sigma = (1 - C_2)^{\frac{1}{2}} \cdot \left(1 - \frac{|A|}{2v_o}\right)^{\frac{1}{2}}.$$

Between the three correlators and the three corresponding inputs of the arithmetic unit 650 there are preferably provided three mean value calculating circuits. These circuits are again formed by accumulators, each of which comprises an adder 344 and delay line 345 for a delay T (or a multiple of T). These mean value calculating circuits enable accumulation of the correlation function values on N successive echographic lines and the formation of the means value thereof before supply to the arithmetic unit. As above, the adders 344 and the delay lines 345 are connected to the sequencer (22, 23) via the connection 104 in order to be reset to zero at regular intervals $N \times T$, the frequency of the resetting to zero imposed by the connection 104 being that of the signals present on the connection 102, divided by N.

Regardless of the construction of the circuit for estimating flow parameters, the output signals of the circuit 330 or 630 are validated or rejected by the discriminator 360, after which the values thus confirmed are applied to the display device 312 via the colour encoding device 370.

The discriminator circuit 360 is indispensable. Actually, outside the flow zones the output signal of the circuit 320 for suppressing fixed echoes is essentially formed by noise. The result supplied by the circuit 330 or 630 for estimating flow parameters which processes this noise is not an indication of a velocity zero, so that it is necessary to validate or reject this result. To this end, the circuit 360 shown in FIG. 8 comprises a series connection of a multiplier 361 which receives the output signal $d_i$ of the circuit 320 for suppressing fixed echoes and which squares this difference signal, a summing device 362 which enables calculation of the local energy of this difference signal according to the formula:

$$E_i(J) = \sum_{k=1}^{k=K} d^2((k+J)\Delta t) \quad (23)$$

a circuit (364, 365) for calculating the mean value which, as in the case of the circuits 344 and 345, is formed by an accumulator which comprises an adder 364 and a delay line 365 for a delay T (or a multiple of T) and which enables calculation of the mean value of the local energy for N activations, that is to say (N−1) differences according to the expression:

$$E(J) = \sum_{i=1}^{i=N-1} E_i(J) \quad (24)$$

before applying the value thus obtained to a validation circuit 460.

The validation circuit 460 comprises a comparator 461 which receives on a first input the output signal of the accumulator (364, 365), or directly that of the summing device 362 when the circuit for calculating the mean value is absent, and on a second input 462 the reference voltage which forms a threshold, the output signal of the comparator then having the logic level 0 or 1, depending on whether the voltage received on its input is lower or higher, respectively, than the reference threshold. Two multipliers 463 and 464, receiving the output signals $V_z$ and $\sigma^2$, respectively, of the circuit 330 or 630 on their forst input, output these two signals, referred to hereinafter as $V'_z$ and $\sigma'^2$ on their respective output or simply output the values zero, depending on whether the validation signal applied to their input by the comparator 461 is 1 or 0, respectively. Actually, outside the true flow zones, the mean energy calculated at the output of the circuit (364, 365) is that of noise only, and can be measured alone in the absence of excitation, in order to determine the appropriate threshold value. However, in the presence of signals returned by the moving targets, the mean energy of the signal $d_i$ is higher than that of the noise alone, thus enabling the validation of the signals supplied by the circuit 330 or 630 for estimating flow parameters.

Figure 8:
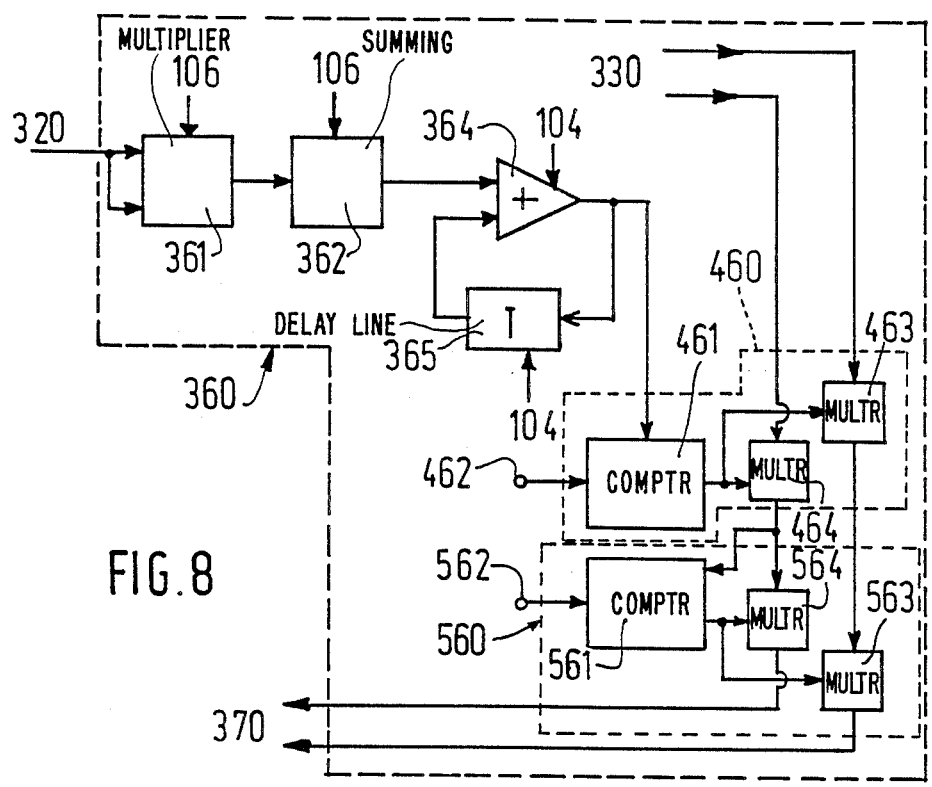
FIG. 8 shows an embodiment of the discriminator circuit of the apparatus shown in FIG. 1.

In an alternative embodiment of the discriminator circuit 360 the variation signal itself may be used as the discrimination signal. Actually, because from one activation to another the noise is uncorrelated, when the calculated variation is large, only noise is present. However, in the presence of returned signals, the variation is substantially smaller and, therefore, a validation circuit 560 is provided with a comparator 561 which receives on a first input the output signal $\sigma'^2$ of the multiplier 462 and on a second input 562 a reference voltage which forms a threshold, and two multipliers 563 and 564 which enable the validation or rejection (as before) of the signals which are now referred to as $V''_z$ and $\sigma''^2$ on the output of these multipliers. It is to be noted that, instead of being situated behind the multipliers 463 and 464 of the validation circuit 460 as shown in FIG. 8, this new validation circuit 560 could be inserted before the first validation circuit, the velocity and variation signals possibly validated thereby then being applied to the corresponding inputs of the multipliers 463 and 464.

After the N excitations, controlled by the signal 102 for the measurement of the flow parameters or the displacement parameters of the structures situated on the axis of the transducer, an electronic or mechanical displacement of the transducer is controlled by the scanning control signal 104. The estimation process is then initiated again in another direction of examination.

The two output signals of the discriminator circuit 360 are applied to the device 370 for storage, scan conversion and colour encoding which also receives, prior to display, the output signal of the amplifier 311 of the processing channel 301. A device of this kind is described, for example in European Patent Application EP-A-0100094. FIG. 3 of this document actually shows, connected between the terminals A, B, C and $E_R$, $E_G$, $E_B$, an example of circuits which may be inserted according to the present invention, the terminal A receiving the conventional echographic signal whilst the terminals B and C receive the characteristic parameters of the moving object being examined. The device 370 and the device 312 thus enable real-time display of flows of displacements superposed on the conventional echographic reflection image.

What is claimed is:

1. In apparatus examining objects by means of ultrasound echography of the type which comprises: means for directing periodic pulses of ultrasound energy onto said objects; means for detecting and generating signals representative of echoes of said energy which are reflected from said objects; means for suppressing from said echo signals echoes which originate from stationary objects to produce moving object echo signals which are representative of echoes which originate only from moving objects; means which correlate said moving object echo signals from two successive periodic pulses and which estimate parameters of flow therefrom; and means for displaying said parameters of flow as a function of the point of origin of said echoes, the improvement comprising a validation circuit which includes:

means which subtract moving object echo signals produced by two successive of said periodic pulses to produce a difference signal therefrom;
   means which calculate the energy in a portion of said difference signal which originates from a local region of the objects being examined; and
   means which compare the calculated energy from said local region with a predetermined threshold energy level and which suppress the display of parameters of flow in said local region if the calculated energy is less than said predetermined threshold energy level.

2. The improvement of claim 1 further comprising means which calculate the mean energy of a series of difference signals representing echoes returned from said local region and wherein the means which compare suppresses the display of flow parameters in the region if the mean energy of said difference signals is less than the predetermined threshold.

3. The improvement of claim 1 or 2 wherein the means which correlate estimate flow velocity in the local region and wherein the validation circuit further includes means which compare the estimated flow velocity in the local region with a predetermined velocity threshold value and which suppress display of the flow parameters in the region if the estimated velocity is less than the threshold.

4. In a device which images blood flow in local regions of a body by cross correlation of successive ultrasound echographic lines reflected from the region, a circuit for suppressing spurious signal displays comprising in combination:

fixed echo cancelling means which filter echoes reflected from stationary objects from the echographic lines;
   means which suppress display of flow information from a local region when the energy content of the difference between two successive lines from the region is less than a threshold energy level; and
   means which suppress display of the flow information from a local regions when estimated flow velocity in said region is less than a threshold velocity.

* * * * *